US008634070B2

United States Patent
Ishihara

(10) Patent No.: US 8,634,070 B2
(45) Date of Patent: Jan. 21, 2014

(54) METHOD AND APPARATUS FOR OPTICALLY INSPECTING A MAGNETIC DISK

(71) Applicant: Hitachi High-Technologies Corporation, Tokyo (JP)

(72) Inventor: Ayumu Ishihara, Saitama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/757,119

(22) Filed: Feb. 1, 2013

(65) Prior Publication Data

US 2013/0258325 A1    Oct. 3, 2013

(30) Foreign Application Priority Data

Mar. 30, 2012   (JP) ................................ 2012-079606

(51) Int. Cl.
*G01N 21/00* (2006.01)
(52) U.S. Cl.
USPC .................. 356/237.2; 356/237.1; 356/237.4; 356/237.5
(58) Field of Classification Search
USPC .......................................... 356/237.1–237.5
See application file for complete search history.

(56) References Cited

U.S. PATENT DOCUMENTS

| | | | | |
|---|---|---|---|---|
| 6,509,965 | B2 * | 1/2003 | Fossey et al. | 356/237.2 |
| 6,657,736 | B1 * | 12/2003 | Finarov et al. | 356/625 |
| 6,903,342 | B2 * | 6/2005 | Chien | 250/341.1 |
| 7,869,024 | B2 * | 1/2011 | Urano et al. | 356/237.2 |
| 8,018,585 | B2 * | 9/2011 | Hariyama et al. | 356/237.2 |
| 8,253,935 | B2 * | 8/2012 | Hariyama et al. | 356/237.2 |
| 2009/0190123 | A1 * | 7/2009 | Hariyama et al. | 356/237.2 |
| 2011/0075139 | A1 * | 3/2011 | Soeda et al. | 356/237.5 |
| 2013/0077092 | A1 * | 3/2013 | Sasazawa et al. | 356/237.5 |

FOREIGN PATENT DOCUMENTS

| | | |
|---|---|---|
| JP | 10-253543 A | 9/1998 |
| JP | 2000-180376 A | 6/2000 |

* cited by examiner

*Primary Examiner* — Sang Nguyen
(74) *Attorney, Agent, or Firm* — Mattingly & Malur, PC

(57) ABSTRACT

In a method and apparatus for optically inspecting a magnetic disk, irradiating the surface of the sample with a light by rotating and moving the sample in the direction orthogonal to the center axis of the rotation, detecting the regular reflection light from the surface of the sample, detecting the scattered light in the vicinity of the regular reflection light from the surface of the sample by separating the scattered light from the regular reflection light, detecting the scattered light scattered in the direction at a higher angle with respect to the normal direction of the surface of the sample, and detecting the defects by processing the detection signal of the regular reflection light, the detection signal of the scattered light in the vicinity of the regular reflection light, and the detection signal of the scattered light in the high angle direction.

12 Claims, 7 Drawing Sheets

$D = \{(2061)+(2062)\} - \{(2063)+(2064)\}$ $D = \{(2061)+(2062)\} - \{(2063)+(2064)\}$

METHOD AND APPARATUS FOR OPTICALLY INSPECTING A MAGNETIC DISK

BACKGROUND

The present invention relates to a method and apparatus for optically inspecting magnetic media (magnetic dicks).

An aluminum (Al) substrate or a glass substrate is used as a substrate for a magnetic disk. As for the glass substrate, crystallized glass (SX) or amorphous glass (MEL) is used according to the application. Further, in each of the types of glass, a plurality of types of glass containing different components are used.

There is a possibility that small concave (pit) defects and small convex (bit) defects may occur on the surface of the glass substrate during the production process. The glass substrate having such small defects is likely to be defined as a defective product in the final inspection process. Thus, it is desirable that such a glass substrate likely to be defined as a defective product should be removed from the line in the initial process of the production line for the purpose of maintaining high production yield.

As for the conventional apparatus for inspecting defect on the surface of a magnetic disk, for example, Japanese Patent Application Laid-Open Publication No. 2000-180376 describes a method of irradiating a magnetic disk as a sample to be inspected with a laser beam, receiving the reflected light and scattered light from the surface of the magnetic disk by a plurality of detectors, and classifying small defects according to the light receiving conditions in each optical receiver. Further, the method also determines the plane continuity of the detected small defects to classify the magnitude of the length of the defects and classify as linear defects and block defects.

Further, Japanese Patent Application Laid-Open Publication No. HEI 10(1998)-253543 discloses a method of irradiating the inspection surface of a substrate to be inspected with a parallel light at the right angle, imaging the reflected light from the inspection surface, detecting concave or convex defects on the inspection surface as part of irregular brightness, converting the number of detected defect pixels of the detected defect into thirty error count values MCF corresponding to the number of missing errors when the substrate is integrated into media, and ranking the quality of the substrate based on the corresponding value MCF.

SUMMARY

The glass substrate with small concave (pit) defects and small convex (bit) defects on the surface is likely to be defined as a defect product in the final inspection process. For this reason, is it desirable to remove such a glass substrate from the line in the initial process of the production line to increase the production yield.

The method described in Japanese Patent Application Laid-Open Publication No. 2000-180376 includes the steps of: detecting the reflected light and scattered light from the surface of the magnetic disk irradiated with a laser beam by a plurality of detectors; extracting small defects by processing the detection signals from the detectors; and classifying the extracted small defects. However, there is no description of the method of detecting small concave (pit) defects and small convex (bit) defects on the surface of the magnetic disk.

Further, in the concave-convex determination method described in Japanese Patent Application Laid-Open Publication No. HEI 10(1998)-253543, the irregular darkness is determined to be convex and the irregular brightness displacement is determined to be concave according to the intensity of the reflected light in the flat part. Further, the size of the defect can be obtained from the number of pixels of the defect imaged by a light receiving element. In this method, for example, when a concave defect filled with contamination (waste) is measured or when a concave portion with a low reflection ratio on the bottom is measured, the phenomenon of reduction in the received light intensity simply occurs. In this case, only the irregular darkness may be detected and erroneously determined to be a convex defect. Further, the method may double count a single large defect over the scan pitch as a plurality of defects.

The present invention is to address the problems in the related art, and provide a method and apparatus for optically inspecting a magnetic disk that can identify concave and convex of defects in order to detect defects as different types of defects including small concave (pit) defects and small convex (bit) defects on a surface of the magnetic disk.

In order to address the above problems, the present invention provides a disk surface inspection apparatus including: a stage unit on which a disk of magnetic media is placed as a sample that can be rotated and moved in the direction orthogonal to the center axis of the rotation; a first illumination unit for irradiating the surface on the front side of the sample placed on the stage unit with a light; a first regular reflection light detection unit for detecting the regular reflection light reflected from the surface on the front side of the sample irradiated with the light by the first illumination unit; a first low angle scattered light detection unit for detecting the scattered light in the vicinity of the regular reflection light reflected from the surface on the front side of the sample irradiated with the light by the first illumination unit, by separating the scattered light from the regular reflection light; a first high angle scattered light detection unit for detecting the scattered light scattered in the direction at a higher angle than the direction of the regular reflection light with respect to the normal direction of the sample, from the sample irradiated with the light by the first illumination unit; and a processing unit for detecting defects on the surface of the sample by processing the output signal from the first regular reflection light detection unit, the output signal from the first low angle scattered light detection unit, and the output signal from the first high angle scattered light detection unit. The regular reflection light detection unit includes a detector having a plurality of detection elements for detecting the regular reflection light reflected from the sample. The processing unit includes a concave-convex defect determination unit for determining concave and convex of the defects on the sample by processing the output signal from the detector having the detection elements in the regular reflection light detection unit.

Further, in order to address the above problems, the present invention provides a method for optically inspecting a magnetic disk. The method includes the steps of: irradiating the front side of a disk as a sample with a light by rotating and moving the sample in the direction orthogonal to the center axis of the rotation; detecting the regular reflection light reflected from the surface of the sample irradiated with the light; detecting the scattered light from the surface of the sample and in the vicinity of the regular reflection light reflected from the surface of the sample irradiated with the light, by separating the scattered light from the regular reflection light; detecting the scattered light scattered in the direction at a higher angle than the direction of the regular reflection light with respect to the normal direction of the surface of the sample, from the surface of the sample irradiated with the light; and detecting defects on the surface of the sample by processing the detection signal of the regular reflection light, the detection signal of the scattered light in the vicinity of the regular reflection light, and the detection signal of the scattered light scattered in the high angle direction. Further, the method also includes the steps of: detecting the regular reflection light reflected from the sample by a detector having a plurality of detection elements; and determining concave and convex of the defects on the sample by processing the output signal from the detector having the detection elements.

According to the aspects of the present invention, it is possible to detect small concave (pit) defects and small convex (bit) defects that occur on the surface of a glass substrate, separately from foreign materials or other defects. As a result, it is possible to increase the production yield by removing the glass substrate with such defects from the line in the initial process of the production line.

These features and advantages of the invention will be apparent from the following more particular description of preferred embodiments of the invention, as illustrated in the accompanying drawings.

DESCRIPTION OF THE PREFERRED EMBODIMENTS

The present invention is an apparatus for inspecting the surface of a glass substrate, by detecting the regular reflection light or scattered light from the substrate that is irradiated with the illumination light, identifying whether the defect on the surface of the glass substrate is concave or convex from the detection signal of the regular reflection light, extracting defect candidates from the detection signal of the scattered light, and classifying the defect type of the extracted defect candidates based on the features of each defect candidate and on the information of identifying concave and convex of the defects.

Figure 1A:
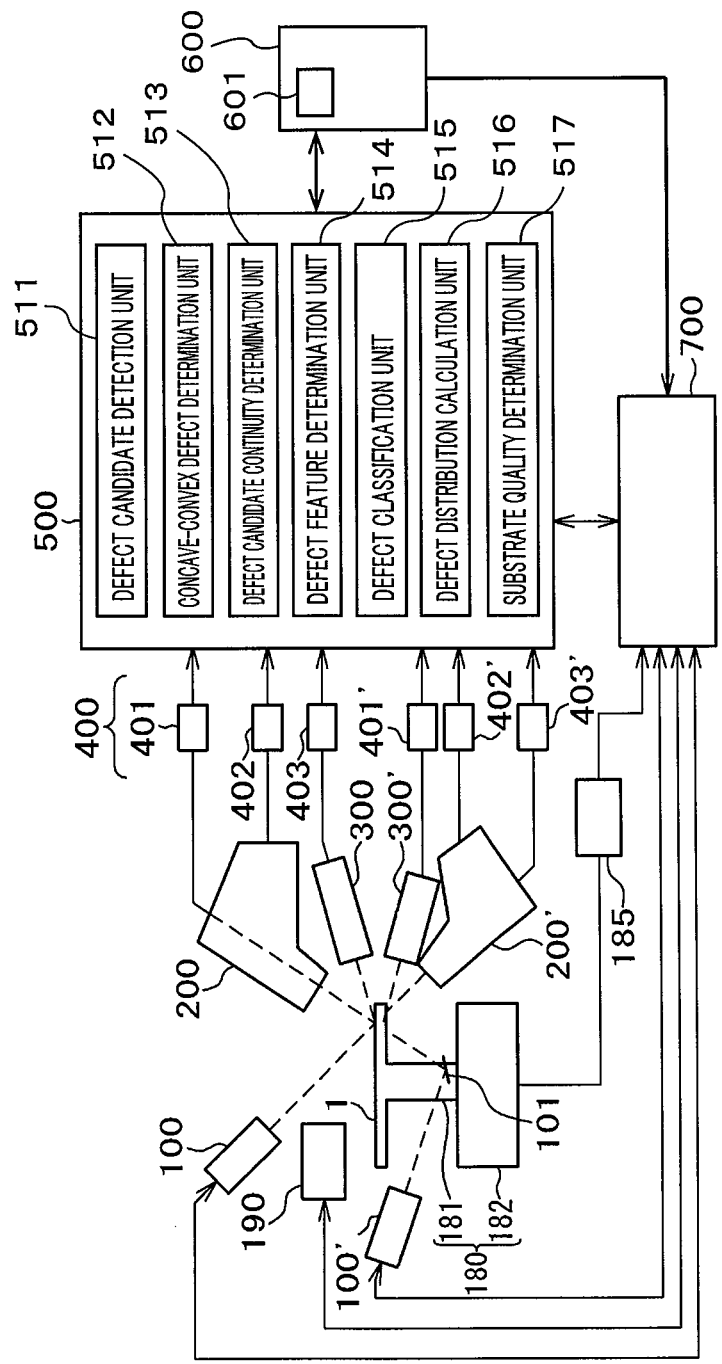
FIG. 1A is a schematic block diagram of an apparatus for optically inspecting a magnetic disk according to a first embodiment of the present invention.

Hereinafter, an embodiment of the present invention will be described with reference to the accompanying drawings. FIG. 1A shows a general configuration of a disk surface defect inspection apparatus 1000 according to the present embodiment. A sample 1 to be inspected is a substrate for a magnetic disk, which is formed from a glass material. The disk surface defect inspection apparatus 1000 inspects the front and back surfaces of the sample 1 at the same time.

The disk surface defect inspection apparatus 1000 includes: an illumination unit 100 for irradiating the surface on the front side of the sample 1 with an illumination light; a low angle detection optical system 200 for collecting light that is regularly reflected or scattered in a low angle direction from the front surface side of the sample 1 irradiated with the illumination light (namely, in the direction at a small angle from the normal direction of the surface of the sample 1); a high angle detection optical system 300 for collecting and detecting light scattered in a high angle direction from the front surface side of the sample 1 (namely, in the direction at a large angle from the normal direction of the surface of the sample 1); an illumination unit 100' for irradiating the back surface side of the sample 1 with an illumination light; a mirror 101 for changing the optical path of the illumination light to irradiate the back side of the sample 1 with the illumination light emitted from the illumination unit 100'; a low angle detection optical system 200' for collecting and detecting light that is regularly reflected and scattered in a low angle direction from the back surface of the sample 1 irradiated with the illumination light (namely, in the direction at a small angle from the normal direction of the surface of the sample 1); a high angle detection optical system 300' for collecting and detecting light scattered in a high angle direction from the back surface of the sample 1 (namely, in the direction at a large angle from the normal direction of the surface of the sample 1); an A/D converter 400 for amplifying analog detection signals, which are output from the low angle detection optical systems 200, 200' and the high angle detection optical systems 300, 300', respectively, as a result of the detection of the regular reflection light and scattered light from the sample 1, and converting analog to digital signals; a processing unit 500 for receiving the signals that are converted by the A/D converter 400 and output from the detectors; an input/output unit 600 for inputting the process conditions of the processing unit 500 and outputting the result of the process; a general control unit 700 for controlling the entire disk surface defect inspection apparatus 1000; and a stage unit 180 on which the sample 1 is placed, which is controlled by a stage control unit 185 to rotate and move the sample 1 in one direction.

The illumination units 100 and 100' include a laser light source for outputting a laser with a desired wavelength, respectively.

Basically, the low angle detection optical systems 200, 200' and the high angle detection optical systems 300, 300' respectively have the same configuration. Thus, the following description will focus on the low angle detection optical system 200 and the high angle detection optical system 300 that inspect the front surface of the sample 1.

Figure 1B:
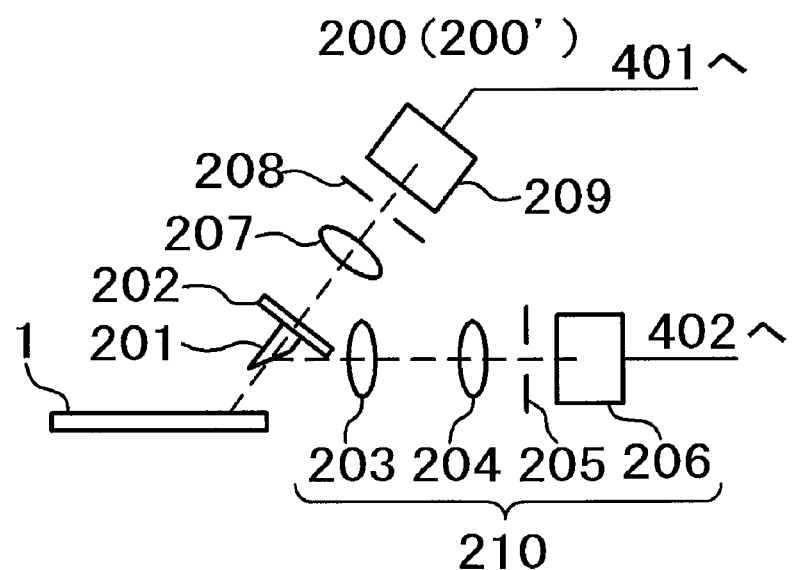
FIG. 1B is a schematic block diagram of a regular reflection light detection optical system, as well as a low angle detection optical system in the apparatus for optically inspecting a magnetic disk, according to the first embodiment of the present invention.

The low angle detection optical system 200 is an optical system for detecting the reflected and scattered light that is reflected and scattered from the surface of the sample 1 irradiated by the illumination unit 100, including the regular reflection light in the low angle direction of the directions indicated by the dotted lines. As shown in FIG. 1B, the low angle detection optical system 200 includes: a mirror 201 for reflecting the regular reflection light travelling in the low angle direction from the surface of the sample 1; a Fresnel lens 202 acting as an objective lens for collecting the scattered light in the vicinity of the regular reflection light that is not reflected by the mirror 201; an objective lens 203 for collecting the regular reflection light reflected by the mirror 201; a converging lens 204 for converging the regular reflection light that is reflected from the sample 1 and collected by the objective lens 203; a pin hole plate 205 for blocking stray light other than the regular reflection light that is converged by the converging lens 204, by allowing the regular reflection light to pass through a pin hole formed on the pin hole plate 205 at the convergence point of the regular reflection light; a regular reflection light detection system 210 including a regular reflection light detector 206 for detecting the regular reflection light passing through the pin hole of the pin hole plate 205; a converging lens 207 for converging the light (the scattered light in the vicinity of the regular reflection light from the sample 1) that is collected by the Fresnel lens 202; a pin hole plate 208 for blocking light other than the light converged by the converging lens 207, by allowing the converged light to pass through a pin hole formed on the pin hole plate 208 at the convergence point of the converging lens 207; and a low angle detector 209 for detecting the light passing through the pin hole plate 208.

Figure 1C:
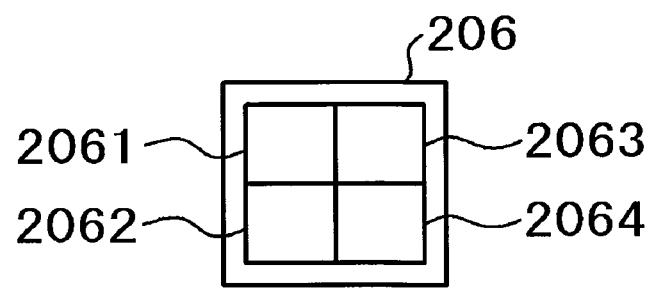
FIG. 1C is a front view of a four-segment sensor of the regular reflection light detection optical system of the apparatus for optically inspecting a magnetic disk, according to the first embodiment of the present invention.

Here, as shown in FIG. 1C, the regular reflection light detector 206 includes a four-segment sensor that is divided into four detection elements with detection surfaces 2061 to 2064. However, the regular reflection light detector 206 is not limited to the four-segment sensor. Other sensors such as a six-segment sensor or an eight-segment sensor may also be used. Further, in FIG. 1C, the detection elements are shown by rectangular shapes, but it is also possible to use a four-segment sensor which is a circle divided into four segments.

Figure 1D:
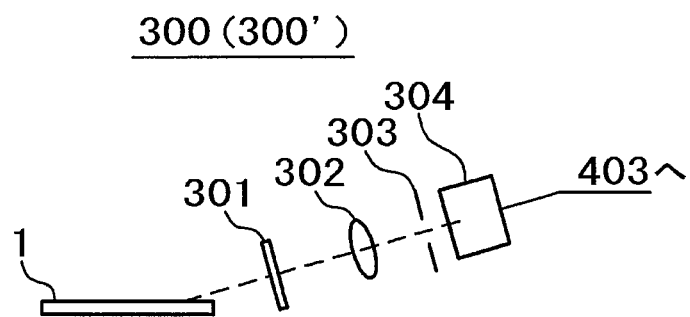
FIG. 1D is a schematic block diagram of a high angle detection optical system of the apparatus for optically inspecting a magnetic disk according to the first embodiment of the present invention.
Figure 1E:
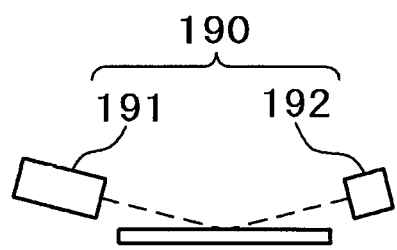
FIG. 1E is a schematic block diagram of a surface displacement measurement unit of the apparatus for optically inspecting a magnetic disk according to the first embodiment of the present invention.

As shown in FIG. 1D, the high angle detection optical system 300 includes: a Fresnel lens 301 acting as an objective lens for collecting the scattered light travelling in the high angle direction, of the light that is emitted from the illumination unit 100 and is reflected and scattered from the surface of the sample 1; a converging lens 302 for converging the light collected by the Fresnel lens 301; a pin hole plate 303 for blocking light other than the light converged by the converging lens 302, by allowing the converged light to pass through a pin hole formed on the pin hole plate 303 at the convergence point of the converging lens 302; and a high angle detector 304 for detecting the light passing through the pin hole plate 303.

The detectors 206, 209, and 304 detect the reflected and scattered light from the front surface of the sample 1, and output analog signals. Then, the analog signals output from the detectors 206, 209, and 304 are amplified and converted from analog to digital signal by the A/D converters 401 to 403 of the A/D converter 400, respectively. Then, the digital signals are input to the processing unit 500. Similarly, the low angle detection optical system 200' and the high angle detection optical system 300' detect the reflected and scattered light from the back surface of the sample 1, and output analog signals. Then, the analog signals output from the low angle detection optical system 200' and the high angle detection optical system 300' are amplified and converted from analog to digital signal by the A/D converters 401' to 403' of the A/D converter 400, respectively. Then, the digital signals are input to the processing unit 500.

The processing unit 500 processes the output signals from the low angle detection optical system 200 and the high angle detection optical system 300 that inspect the front surface of the sample 1, as well as the output signals from the low angle detection optical system 200' and the high angle detection optical system 300' that inspect the back surface of the sample 1. Both processes on the front and back surfaces of the sample 1 are the same, so that the following description will focus on the process of signals output from the low angle detection optical system 200 and the high angle detection optical system 300 that inspect the front surface of the sample 1.

The processing unit 500 includes: a defect candidate detection unit 511 for detecting defect candidates in response to the signals that are output from the detectors 206, 209, and 304 and converted from analog to digital signal by the A/D converter 400; a defect candidate continuity determination unit 512 for determining the connection and continuity of the defect candidates detected by the defect candidate detection unit 151, by using the position information of each of the detected defect candidates on the sample 1 that is obtained by the stage control unit 185 and the stage unit 180; a concave-convex defect determination unit 513 for determining concave and convex defects on the surface of the sample 1 in response to the detection signal from the regular reflection light detector 206; a defect feature extraction unit 514 for extracting the defect features of each of the defect candidates, of which the connection and continuity are determined by the defect candidate continuity determination unit 512, and of which the concave or convex shape is determined by the concave-convex defect determination unit 513; a defect classification unit 515 for classifying the defect candidates into different defect types based on the features of the individual defect candidates that are obtained by the defect feature extraction unit 514; a defect distribution calculation unit 516 for obtaining the distribution of the defect candidates on the sample 1 for each defect type classified by the defect classification unit 515; and a substrate quality determination unit 517 for determining whether the sample 1 is good or not based on the number of defects and distribution for each of the defect types obtained by the defect distribution calculation unit 516.

The processing unit 500 is connected to the input/output unit 600 including a display screen 601 to input the inspection conditions and output the result of the inspection. Further, the processing unit 500 and the input/output unit 600 are connected to the general control unit 700. The general control unit 700 controls the stage control unit 185 for driving and controlling the stage unit 180 including a spindle unit 181 for rotating the sample 1 placed on the stage unit 180, and a linear stage 182 capable of moving at least in one axis direction within the plane where the sample 1 rotates. The general control unit 700 also controls the illumination unit 100, the processing unit 500, and the input/output unit 600.

Figure 2:
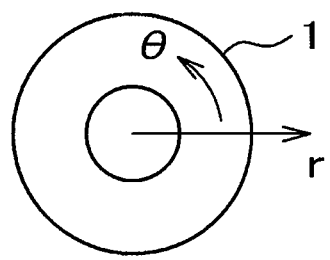
FIG. 2 is a plan view of a disk of magnetic media as a sample.

With the configuration described above, the stage control unit 185 is controlled by the general control unit 700 to drive and control the spindle unit 181 and the linear stage 182 of the stage unit 180. In this way, as shown in FIG. 2, the sample 1 placed on the stage unit 180 is rotated in the θ direction and starts moving in the direction orthogonal to the rotation center 10, namely, in the radial (r) direction of the sample 1 at a constant speed.

In this state, the surface of the sample 1 rotating on the stage unit 180 is irradiated with a laser beam from the illumination unit 100. Of the light reflected and scattered by the surface of the sample 1 and travelling in the direction of the Fresnel lens 201, the regular reflection light is detected by the regular reflection light detector 206 and the scattered light in the vicinity of the regular reflection light is detected by the low angle detector 209. Further, the scattered light from the surface of the sample 1 in the direction of the Fresnel lens 301 of the high angle detection optical system 300, is detected by the first high angle detector 304.

Such an inspection is performed by rotating the sample 1 and moving it straight. At this time, the surface of the sample 1 is inspected from the inner periphery to the outer periphery of the sample 1 in a spiral manner. In this way, it is possible to inspect the entire surface on the front side of the sample 1.

During the inspection, in the surface displacement measurement unit 190, the reflected light of the light beam incident on the surface of the sample 1 from a projector 191 is detected by a detector 192 including a plurality of pixels. Then, the detector 192 outputs a detection signal according to the detection position of the reflected light. The signal output from the detector 192 is processed by the general control unit 700 to obtain the variation in the height of the surface of the sample 1. Then, the height of the low angle detection optical system 200 and the height of the high angle detection optical system 300 with respect to the surface of the sample 1 are controlled by an autofocus unit, not shown, according to the obtained variation. In this way, stable inspection can be maintained.

Note that in this embodiment, the pin hole plates 205, 208, and 303 are used for the low angle detection optical system 200 and the high angle detection optical system 300, respectively, in order to block stray light. However, when a polarizing plate is inserted in the middle of the optical path of the laser beam emitted from the illumination source 100 to irradiate the sample 1 with a polarized light, it is possible to use a polarizing filter instead of the pin hole plates 205, 208, and 303. Also, when a single wavelength laser is used as the laser emitted from the illumination source 100, it is possible to use a wavelength selective filter instead of the pin hole plates 205, 208, and 303. Further, it is also possible to use both the polarizing filter and the wavelength selective filter to allow light having specific polarization components to pass through.

Figure 3:
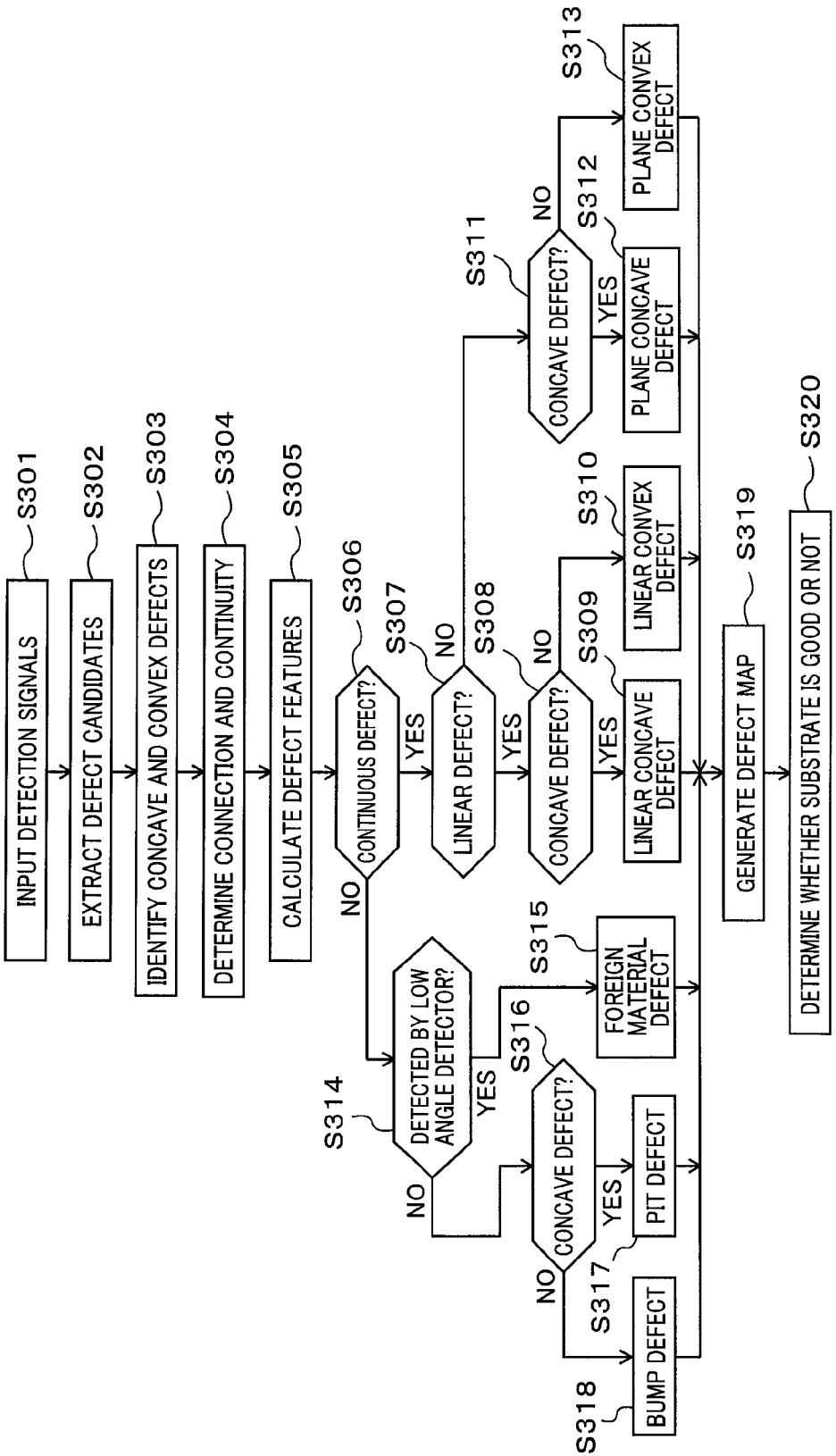
FIG. 3 is a flow chart showing the process flow of a method for optically inspecting a magnetic disk, according to the first embodiment of the present invention.

Next, the procedure of the process of the signals output from the detectors 206, 209, 304 and input to the processing unit 500 will be described with reference to FIG. 3.

The detection signals output from the detectors 206, 209, and 304 are converted from analog to digital signal by the A/D converters 401 to 403, respectively, and input to the processing unit 500 (S301).

When the detection signals are input to the processing unit 500, the defect candidate extraction unit 511 first compares the level of the signals input from the A/D converters 401 to 403 with a predetermined threshold. Then, the defect candidate extraction unit 511 extracts signals of a level exceeding the threshold as defect candidates, in conjunction with the position information of the defect candidates on the sample 1 that is obtained from the detection system (not shown) of the stage control unit 185 and the stage unit 180 (the rotation angle (θ) information of the stage unit 180 as well as the substrate radius (r) direction position information) (S302).

The concave-convex defect determination unit 152 determines concave and convex defects on the surface of the sample 1 in response to the detection signal from the regular reflection light detector 115 with respect to the defect candidates extracted in S302 (S303).

Here is the description of the process of determining concave and convex defects on the surface of the sample 1 in response to the detection signals from the regular reflection light detector 115.

Figure 4A:
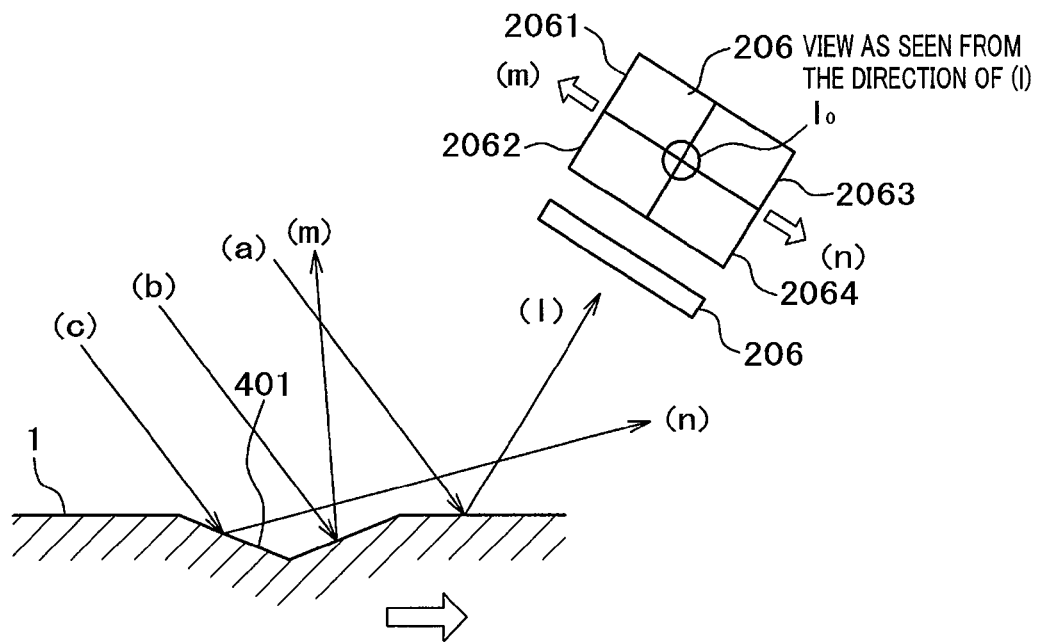
FIG. 4A is a cross-sectional view of the sample with a concave defect on the surface to be inspected, showing the direction in which the regular reflection light is reflected from each part of the surface to be inspected, and showing the projection position of the regular reflection light on the surface of the four-segment sensor.

FIG. 4A shows the relationship between the reflected light from the surface of the sample 1 and the detector 206, when a concave defect 401 is present on the surface of the sample 1. It is assumed that the sample 1 is rotated in the arrow direction and that the area of the sample 1 irradiated with the illumination light sequentially changes from (a) to (c).

First, in FIG. 4A, (a) shows the state in which the flat part of the sample 1 is irradiated with the illumination light and the regular reflection light in the direction of (l) is detected by detector 206 in the center of the detection surface divided into four regions. In other words, the regular reflection light is equally detected in the four detection surfaces 2061 to 2064 of the detector 206. Then, the detection surfaces 2061 to 2064 of the detector 206 output signals. At this time, the difference between the sum of the outputs of the detection surfaces 2061 and 2062, and the sum of the outputs of the detection surfaces 2063 and 2064: D {(2061)+(2062)}−{(2063)+(2064)} is zero.

Next, (b) shows the state in which the inclined surface on the right side of the concave defect 401 on the surface of the sample 1 is irradiated with the illumination light and the regular reflection light is directed in the direction of (m). At this time, the regular reflection light in the direction (m) is reflected in the direction of the arrow m, passing over the detection surfaces 2061 and 2062. As a result, the regular reflection light is deviated from the four detection surfaces of the detector 206. At this time, the difference D between the sum of the outputs of the detection surfaces 2061 and 2062, and the sum of the outputs of the detection surfaces 2063 and 2064, once rises to the peak level on the plus side and then falls back to zero.

Further, (c) shows the state in which the inclined surface on the left side of the concave defect 401 on the surface of the sample 1 is irradiated with the illumination light and the regular reflection light is directed in the direction of (n). At this time, the regular reflection light in the direction of (n) is reflected in the direction of the arrow n, passing over the detection surfaces 2061 and 2062. As a result, the regular reflection light is deviated from the four detection surfaces of the detector 206. At this time, the difference D between the sum of the outputs of the detection surfaces 2061 and 2062, and the sum of the outputs of the detection surfaces 2063 and 2064, is once the peak level on the minus side and then back to zero.

Figure 4B:
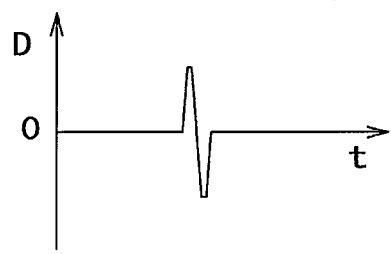
FIG. 4B is a graph of the waveform of a signal output from a regular reflection light detector when the surface to be inspected with a concave defect is scanned with an illumination light.

In FIG. 4A, when the area of the sample 1 irradiated with the illumination light sequentially changes from (a) to (c), the difference D between the sum of the outputs of the detection surfaces 2061 and 2062, and the sum of the outputs of the detection surfaces 2063 and 2064 is expressed by a graph as shown in FIG. 4B. In other words, when the concave defect 401 shown in FIG. 4A is irradiated with the illumination light in the directions (a) to (c) in this order, the difference D between the outputs of the individual detection surfaces of the detector 206 has a signal waveform that once rises to the peak on the plus side from zero and falls back to the zero level, and then has the peak on the minus side and back to zero again.

Figure 5A:
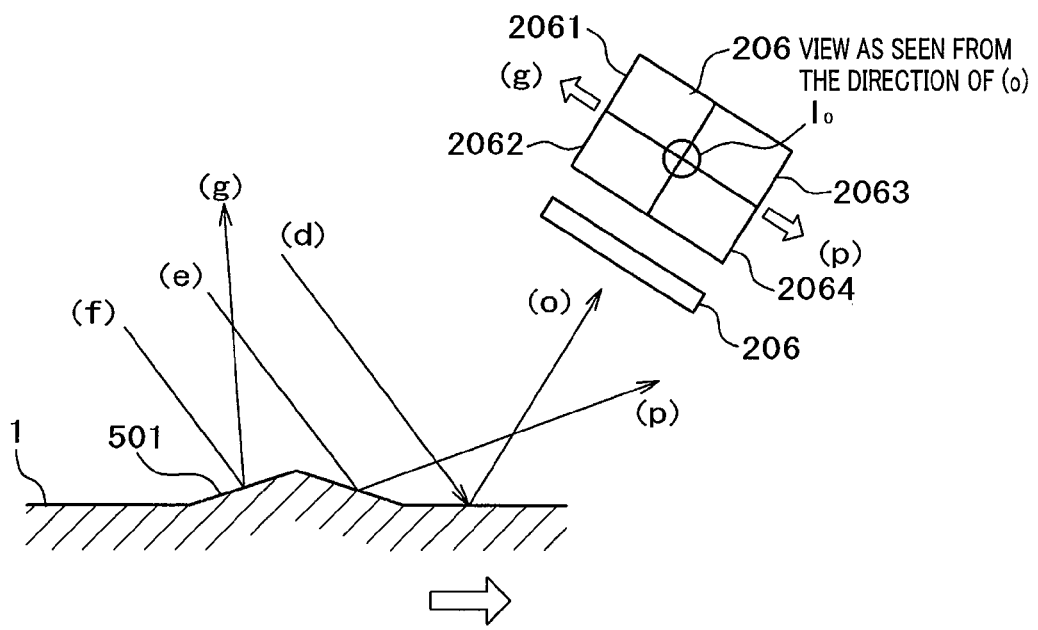
FIG. 5A is a cross-sectional view of the sample with a convex defect on the surface to be inspected, showing the direction in which the regular reflection light is reflected from each part of the surface to be inspected, and showing the projection position of the regular reflection light on the surface of the four-segment sensor.

FIG. 5A shows the relationship between the reflected light from the surface of the sample 1 and the detector 206, when a convex defect 501 is present on the surface of the sample 1. It is assumed that the sample 1 is rotated in the arrow direction and that the area of the sample 1 irradiated with the illumination light changes from (d) to (f).

First, in FIG. 5A, (d) shows the state in which the flat part of the sample 1 is irradiated with the illumination light and the regular reflection light in the direction of (o) is detected by detector 206 in the center of the detection surface divided into four regions. In other words, the regular reflection light is equally detected in the four detection surfaces 2061 to 2064 of the detector 206. Then, the detection surfaces 2061 to 2064 of the detector 206 output signals. At this time, the difference between the sum of the outputs of the detection surfaces 2061 and 2062, and the sum of the outputs of the detection surfaces 2063 and 2064: {(2061)+(2062)}−{(2063)+(2064)} is zero.

Next, (e) shows the state in which the inclined surface on the right side of the convex defect 501 on the surface of the sample 1 is irradiated with the illumination light, and the regular reflection light is directed in the direction of (p). At this time, the regular reflection light in the direction (p) is reflected in the direction of the arrow (p), passing over the detection surfaces 2063 and 2064. As a result, the regular reflection light is deviated from the four detection surfaces of the detector 206. At this time, the difference D between the sum of the outputs of the detection surfaces 2061 and 2062, and the sum of the outputs of the detection surfaces 2063 and 2064, is once the peak level on the minus side and then back to zero.

Further, (f) shows the state in which the inclined surface on the left side of the convex defect 501 on the surface of the sample 1 is irradiated with the illumination light, and the regular reflection light is directed in the direction of (g). At this time, the regular reflection light in the direction of (g) is reflected in the direction of the arrow g, first passing over the detection surfaces 2063 and 2064 and then passing over the detection surfaces 2061 and 2062. As a result, the regular reflection light is deviated from the four detection surfaces of the detector 206. At this time, the difference D between the sum of the outputs of the detection surfaces 2061 and 2062, and the sum of the output of the detection surfaces 2063 and 2064 is once the peak level on the plus side and then back to zero.

Figure 5B:
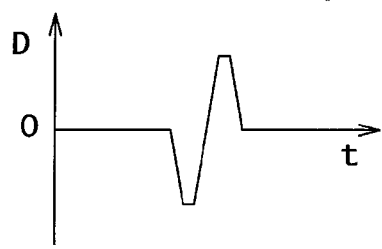
FIG. 5B is a graph of the waveform of a signal output from the regular reflection light detector when the surface to be inspected with a convex defect is scanned with an illumination light.

In FIG. 5A, when the area of the sample 1 irradiated with the illumination light sequentially changes from (d) to (f), the difference D between the sum of the outputs of the detection surface 2061 and 2062, and the sum of the outputs of the detection surfaces 2063 and 2064 is expressed by a graph as shown in FIG. 5B. In other words, when the convex defect 501 shown in FIG. 5A is irradiated with the illumination light in the directions (d) to (f) in this order, the difference D between the outputs of the individual detection surfaces of the detector 206 has a signal waveform that once falls to the peak on the minus side from zero and back to the zero level, then raising to the peak on the plus side and falling to zero again.

As described above, it is possible to determine whether the detected defect is a concave defect or a convex defect, by monitoring the difference D of the outputs of the individual detection surfaces of the detector 206 and by monitoring the signal waveform.

With respect to the defect candidates of which the concave or convex shape is determined in S303, the connection and continuity of the individual defect candidates are determined by the defect candidate continuity determination unit 153, based on the position information on the sample 1 that is obtained in S302 and on the concave/convex information obtained in S303 (S304).

When the connection and continuity are found in the defect candidates, the particular defect candidates are treated as a single defect in the following process.

With respect to the defect candidates in which the connection and continuity are determined in the defect candidate continuity determination unit 153, the defect features such as the dimensions (length in the r direction, length in the θ direction, and width of the defect) and the area of the defect, are calculated in the defect candidate feature calculation unit 154 (S305). At this time, the defect candidates in which the connection and continuity are determined by the defect candidate continuity determination unit 153, are treated as a single defect when their features are calculated.

Finally, the defect classification unit 155 checks whether the defect whose features are calculated is a continuous defect (S306). When it is determined to be a continuous defect, the defect classification unit 155 checks whether it is a linear defect (S307). If the continuous defect does not extend in the plane, the defect classification unit 155 determines whether the particular defect is a concave defect (S308). When the particular defect is a concave defect, it is determined to be a linear concave defect (S309). When the particular defect is a convex defect, it is determined to be a linear convex defect (S310).

On the other hand, if the continuous defect is not a linear defect in S307, the defect classification unit 155 determines that the continuous defect extends in the plane, and determines whether it is a concave defect or not (S311). When the particular defect is a concave defect, it is determined to be a planar concave defect (S312). When the particular defect is a convex defect, it is determined to be a planar convex defect (S313).

Further, when it is determined that the defect is not a continuous defect in S306, the defect classification unit 155 checks whether the particular defect is also detected by the low angle detector 209 (S314). When the particular defect is also detected by the low angle detector 209, it is determined to be a foreign material defect (S315). When the particular defect is not detected by the low angle detector 209, the defect classification unit 155 determines whether it is a concave defect or not (S316). When the particular defect is a concave defect, it is determined to be a pit defect, which is a small dent on the surface of the sample 1 (S317). When the particular defect is a convex defect, it is determined to be a bump defect, which is a small protrusion on the surface of the sample 1 (S318).

Next, the defect distribution calculation unit 516 obtains the number and distribution of the defects on the sample 1 of each type classified by the defect classification unit 515. Then the defect distribution calculation unit 516 generates a defect map for each defect type (S319).

Finally, the types of defects classified by the defect classification unit 515 in S306 to S318, as well as the number of defects for each defect type are compared with a predetermined reference value, to determine whether the sample (substrate) 1 is good or not (S320).

The input/output unit 600 receives the information of the defect map for each defect type that is generated in the defect distribution calculation unit 516 in S319 from the processing unit 500. Then, the input/output unit 600 displays the result of the inspection on the display screen 601, for example, as shown in FIG. 6.

Figure 6:
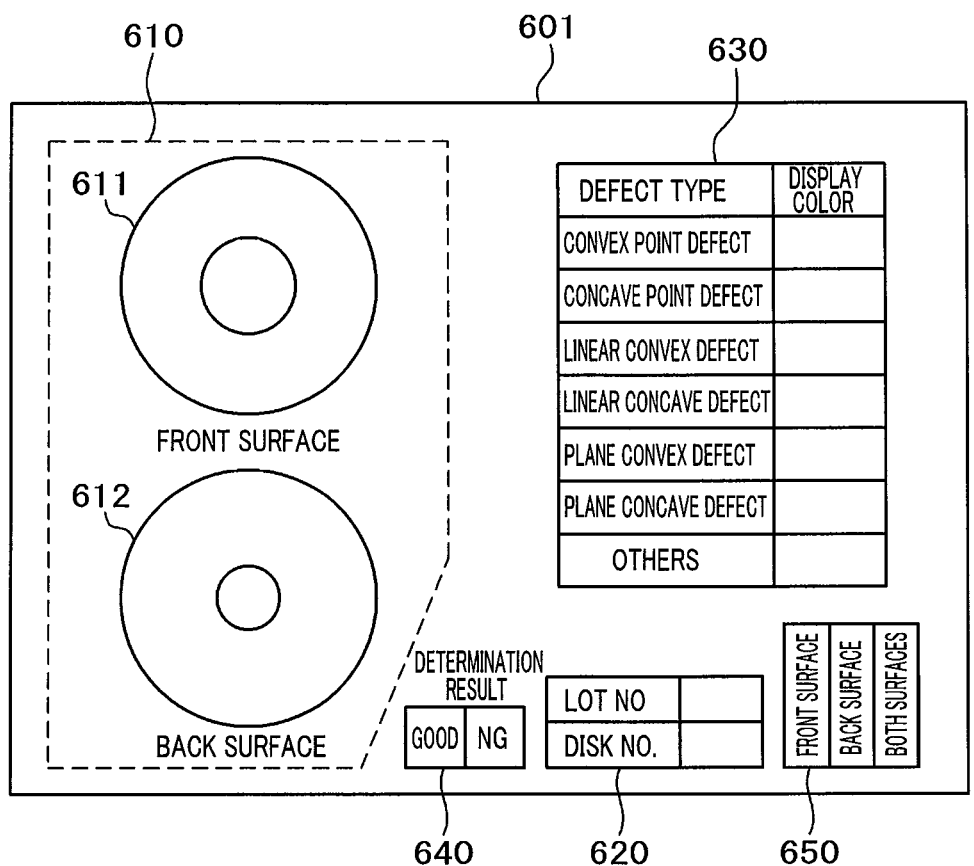
FIG. 6 is a front view of a display screen on which the result of the inspection is output, according to the first embodiment of the present invention.

FIG. 6 is an example of the inspection result displayed on the display screen 601 of the input/output unit 600. On the display screen 601, there is a map display area 610 in which the distribution of the defects on the front surface of the sample 1 is displayed in a defect map 611, and in which the distribution of the defects on the back surface of the sample 1 is displayed in a defect map 612. The display screen 601 also includes a list 630 of the display color for each of the defect types displayed in the defects maps 611 and 612. When a specific defect type is selected by a pointer (not shown) on the list 630, the defects corresponding to the defect type selected on the defect maps 611, 612 are highlighted than the other defects. Further, on the display screen 601, the lot number in the production line of the sample 1 currently displayed in the map display area 610, as well as the disk number representing the sample 1 are displayed in a display field 620.

Further, on the display screen 601, a display area selection button 650 is displayed to select the face of the sample to be displayed on the map display area 610. In this way, it is possible to select which face of the sample is displayed on the map display area 610 from the front surface, the back surface, and both surfaces. FIG. 6 shows the display when both surfaces are selected. Further, the quality determination result of the sample (substrate) 1, which is determined by the substrate quality determination unit 517 in S320, is displayed in the determination result display field 640.

According to the present embodiment, it is possible to determine concave and convex of the defects, which has been difficult to do in the past. As a result, it is possible to detect defects and identify the difference in the type of the defects between bump defects and pit defects and between linear concave defects and linear convex defects.

Note that in the illustrated embodiment, it is assumed that the front and back surfaces of the sample 1 are inspected at the same time as shown in FIG. 1A, but the present invention is not limited to this embodiment. It is also possible to inspect each surface of the sample 1. In other words, the inspection apparatus can first inspect the surface on the front side, and turns the sample 1 over to inspect the surface on the back side, which is now the upper side, by using the illumination unit 100, the low angle detection optical system 200, and the high angle detection optical system 300 that inspect the front surface of the sample 1 shown in FIG. 1A.

While the invention made by the inventors has been described in detail with reference to the preferred embodiment, it will be understood that the present invention is not limited to the illustrated embodiment and various modifications and changes may be made thereto without departing from the spirit and scope of the invention. In other words, the present invention may also include an embodiment in which part of the configuration (step) described in the illustrated embodiment is replaced by a step or unit having the equivalent function thereof, or an embodiment in which part of the unpractical function is omitted.

The invention claimed is:

1. A disk surface inspection apparatus comprising:
a stage unit on which a disk of magnetic media is placed as a sample that can be rotated and moved in a direction orthogonal to a center axis of rotation;
a first illumination unit for irradiating a front surface on a front side of the sample placed on the stage unit with light;
a first regular reflection light detection unit for detecting regular reflection light reflected from the front surface on the front side of the sample irradiated with the light by the first illumination unit;
a first low angle scattered light detection unit for detecting scattered light in the vicinity of the regular reflection light reflected from the front surface on the front side of the sample irradiated with the light by the first illumination unit, by separating the scattered light from the regular reflection light;
a first high angle scattered light detection unit for detecting scattered light scattered in a direction at a higher angle than the direction of the regular reflection light with respect to a normal direction of the sample, from the sample irradiated with the light by the first illumination unit;
a second illumination unit for irradiating a back surface on the back side of the sample placed on the stage unit with light;
a second regular reflection light detection unit for detecting regular reflection light reflected from the back surface on the back side of the sample irradiated with the light by the second illumination unit;
a second low angle scattered light detection unit for detecting scattered light in the vicinity of the regular reflection light reflected from the back surface on the back side of the sample irradiated with the light by the second illumination unit, by separating the scattered light from the regular reflection light;
a second high angle scattered light detection unit for detecting scattered light scattered in the direction at a higher angle than the direction of the regular reflection light reflected from the back surface on the back side of the sample with respect to the normal direction of the sample, from the back surface on the back side of the sample irradiated with the light by the second illumination unit; and
a processing unit for detecting defects on the front surface of the sample by processing an output signal from the first regular reflection light detection unit, an output signal from the first low angle scattered light detection unit, and an output signal from the first high angle scattered light detection unit, and detecting defects on the back surface of the sample by processing an output signal from the first regular reflection light detection unit, an output signal from the first low angle scattered light detection unit, and an output signal from the first high angle scattered light detection unit,
wherein the regular reflection light detection unit includes a detector having a plurality of detection elements to detect the regular reflection light reflected from the front side of the sample, and
wherein the processing unit includes a concave-convex defect determination unit for determining concave and convex features of the defects on the sample by processing the output signal from the detector having the detection elements in the regular reflection light detection unit.

2. The apparatus for optically inspecting a magnetic disk according to claim 1,
wherein the processing unit further includes a defect classification unit for classifying the defects detected on the sample, and
wherein the defect classification unit classifies the detected defects on the sample into a plurality of types of defects including a bump defect which is a protrusion on the front surface of the sample, as well as a pit defect which is a dent on the front surface of the sample, by using the result of determining concave and convex features of the defects on the sample by the concave-convex defect determination unit.

3. The apparatus for optically inspecting a magnetic disk according to claim 1,
wherein the defect classification unit of the processing unit classifies the detected defects on the sample into a plurality of types of defects including a bump defect which is a protrusion on the front surface of the sample, as well as a foreign material defect on the front surface of the sample, by using the result of determining concave and convex features of the defects on the sample by the concave-convex defect determination unit, the output signal from the first low angle scattered light detection unit, and the output signal from the first high angle scattered light detection unit.

4. The apparatus for optically inspecting a magnetic disk according to claim 1,
wherein the first low angle scattered light detection unit includes a Fresnel lens for collecting scattered light in the vicinity of the regular reflection light reflected from the front surface of the sample.

5. A method for optically inspecting front and back surfaces of a magnetic disk at the same time, comprising the steps of:
irradiating the front surface on the front side and the back surface on the back side of the magnetic disk as a sample with lights, by rotating and moving the sample in a direction orthogonal to a center axis of the rotation;
detecting regular reflection lights reflected from the front surface and the back surface of the sample irradiated with the lights with first and second regular light detectors;
detecting scattered lights in the vicinity of regular reflection lights reflected from the front surface and the back surface of the sample irradiated with the lights, by separating the scattered lights from the regular reflection lights, with first and second low angle detectors;
detecting scattered lights scattered in a direction at a higher angle than a direction of the regular reflection lights with respect to normal directions of the front and back surfaces of the sample, from the front surface and back surface of the sample irradiated with the lights, with first and second high angle detectors; and
detecting defects on the front surface and back surface of the sample by processing, with a processing unit, detection signals of the regular reflection lights, detection signals of the scattered lights in the vicinity of the regular reflection lights, and detection signals of scattered lights scattered in the high angle direction,
the method further including the steps of:
detecting the regular reflection light reflected from the front surface of the sample by the first regular light detector having a plurality of detection elements; and
determining concave and convex features of the defects on the sample by processing an output signal from the first regular light detector having the detection elements.

6. The method for optically inspecting a magnetic disk according to claim 5,
wherein the method includes a step of classifying the detected defects on the sample into a plurality of types of defects including a bump defect which is a protrusion on the front surface of the sample, as well as a pit defect which is a dent on the front surface of the sample, by using a result of determining concave and convex features of the defects on the sample.

7. The method for optically inspecting a magnetic disk according to claim 5,
wherein the method includes a step of classifying the detected defects on the sample into a plurality of types of defects including a bump defect which is a protrusion on the front surface of the sample, as well as a foreign material defect on the front surface of the sample, by using a result of determining concave and convex features of the defects on the sample, the detection signal of the scattered lights in the vicinity of the regular reflection lights and separated from the regular reflection lights, and the detection signal of the scattered lights scattered in the high angle direction.

8. The method for optically inspecting a magnetic disk according to claim 5,
wherein the scattered lights scattered in the high angle direction are detected by collecting the scattered lights in the vicinity of the regular reflection lights reflected from the front surface of the sample by using a Fresnel lens.

9. A disk surface inspection apparatus comprising:
a stage unit on which a disk of magnetic media is placed as a sample that can be rotated and moved in the direction orthogonal to the center axis of the rotation;
a first illumination unit for irradiating a surface on a front side of the sample placed on the stage unit with a light;
a first regular reflection light detection unit for detecting a regular reflection light reflected from the surface on the front side of the sample irradiated with the light by the first illumination unit;
a first low angle scattered light detection unit for detecting a scattered light in the vicinity of the regular reflection light reflected from the surface on the front side of the sample irradiated with the light by the first illumination unit, by separating the scattered light from the regular reflection light;
a first high angle scattered light detection unit for detecting a scattered light scattered in a direction at a higher angle than the direction of the regular reflection light with respect to a normal direction of the sample, from the sample irradiated with the light by the first illumination unit; and
a processing unit for detecting defects on the surface of the sample by processing an output signal from the first regular reflection light detection unit, an output signal from the first low angle scattered light detection unit, and an output signal from the first high angle scattered light detection unit,
wherein the regular reflection light detection unit includes a detector having a plurality of detection elements to detect the regular reflection light reflected from the sample, and
wherein the processing unit includes a concave-convex defect determination unit for determining concave and convex features of the defects on the sample by processing a difference signal calculated from the output signal from the detector having the detection elements in the regular reflection light detection unit by adding output signals from a first half of the detection elements and adding outputs signals from a second half of the detection elements and then calculating the difference signal between the output signals of the added first half and the output signals of the added second half.

10. The apparatus for optically inspecting a magnetic disk according to claim 9,
wherein the processing unit further includes a defect classification unit for classifying the defects detected on the sample, and
wherein the defect classification unit classifies the detected defects on the sample into a plurality of types of defects including a bump defect which is a protrusion on the front surface of the sample, as well as a pit defect which is a dent on the front surface of the sample, by using the result of determining concave and convex features of the defects on the sample by the concave-convex defect determination unit.

11. The apparatus for optically inspecting a magnetic disk according to claim 9,
   wherein the defect classification unit of the processing unit classifies the detected defects on the sample into a plurality of types of defects including a bump defect which is a protrusion on the front surface of the sample, as well as a foreign material defect on the front surface of the sample, by using the result of determining concave and convex features of the defects on the sample by the concave-convex defect determination unit, the output signal from the first low angle scattered light detection unit, and the output signal from the first high angle scattered light detection unit.

12. The apparatus for optically inspecting a magnetic disk according to claim 9,
   wherein the first low angle scattered light detection unit includes a Fresnel lens for collecting scattered light in the vicinity of the regular reflection light reflected from the front surface of the sample.

\* \* \* \* \*